US006948522B2

(12) United States Patent

Newbrough et al.

(10) Patent No.: US 6,948,522 B2
(45) Date of Patent: Sep. 27, 2005

(54) RECONSTITUTION DEVICE AND METHOD OF USE

(75) Inventors: Jerry W. Newbrough, Zion, IL (US); James S. Slepicka, Spring Grove, IL (US); Arnold C. Bilstad, Deerfield, IL (US); John Mark DeFoggi, Waukegan, IL (US); Marianne M. Boschelli, Spring Grove, IL (US); Alice M. Jandrisits, Des Plaines, IL (US); Bihong Wu, Santa Clarita, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/457,283

(22) Filed: Jun. 6, 2003

(65) Prior Publication Data

US 2004/0249341 A1 Dec. 9, 2004

(51) Int. Cl.[7] ............................ B65B 1/04; F61L 37/28; A61M 5/00; A61B 19/00

(52) U.S. Cl. ....................... 137/550; 137/558; 137/575; 251/179.5; 604/411; 604/410; 604/405; 141/329

(58) Field of Search ................................ 137/575, 512, 137/550, 588; 251/149.5; 604/236, 414, 191, 82, 86, 126, 122, 405, 246, 284, 410, 523; 141/309, 329, 59; 261/121.1

(56) References Cited

U.S. PATENT DOCUMENTS

| | | | |
|---|---|---|---|
| 2,584,397 | A | 2/1952 | Pitman |
| 3,343,538 | A | 9/1967 | Morley |
| 3,941,171 | A | 3/1976 | Ogle |
| 4,038,981 | A | 8/1977 | LeFevre et al. |
| 4,246,932 | A | 1/1981 | Raines |
| 4,252,159 | A | 2/1981 | Maki |
| 4,378,013 | A | 3/1983 | LeFevre et al. |
| 4,401,432 | A | 8/1983 | Schwartz |
| 4,433,974 | A | 2/1984 | Bischof |
| 4,434,820 | A | 3/1984 | Glass |
| 4,516,967 | A | 5/1985 | Kopfer |
| 4,543,101 | A | 9/1985 | Crouch |
| 4,564,054 | A | 1/1986 | Gustavsson |
| 4,568,346 | A | 2/1986 | van Dijk |
| 4,576,211 | A | 3/1986 | Valentini et al. |
| 4,675,020 | A | 6/1987 | McPhee |
| 4,715,851 | A | 12/1987 | Geisser et al. |
| 4,722,733 | A | 2/1988 | Howson |
| 4,729,401 | A | 3/1988 | Raines |
| 4,768,568 | A | 9/1988 | Fournier et al. |
| 4,787,898 | A | 11/1988 | Raines |
| 4,834,149 | A | 5/1989 | Fournier et al. |
| 4,856,567 | A | 8/1989 | Cosmai |
| 4,883,483 | A | 11/1989 | Lindmayer |
| 4,900,322 | A | 2/1990 | Adams |

(Continued)

FOREIGN PATENT DOCUMENTS

| | | |
|---|---|---|
| EP | 0884 041 | 12/1988 |
| EP | 0570 939 | 11/1993 |

(Continued)

*Primary Examiner*—Nicholas D. Lucchesi
*Assistant Examiner*—Roz Maiorino
(74) *Attorney, Agent, or Firm*—Jeffrey Nichols

(57) ABSTRACT

A reconstitution device is disclosed and includes a first container receiver having a first component cannula disposed therein, the first component cannula having a withdrawal port and a first transfer port formed thereon, a second container receiver having a second component cannula disposed thereon, the second component cannula having a vent port and a second transfer port formed thereon, a device body coupling the first container receiver to the second container receiver and having a transfer lumen formed therein, the transfer lumen in fluid communication with the first and second transfer ports, a selectively sealing interface secured to the device body and in fluid communication with the withdrawal port, and a venting member in communication with the vent port through a vent lumen.

17 Claims, 7 Drawing Sheets

U.S. PATENT DOCUMENTS

| | | | | | |
|---|---|---|---|---|---|
| 4,927,423 | A | | 5/1990 | Malborg | |
| 4,936,841 | A | | 6/1990 | Aoki et al. | |
| 5,045,081 | A | | 9/1991 | Dysarz | |
| 5,114,411 | A | | 5/1992 | Haber et al. | |
| 5,188,615 | A | | 2/1993 | Haber et al. | |
| 5,304,165 | A | | 4/1994 | Haber et al. | |
| 5,330,426 | A | | 7/1994 | Kriesel et al. | |
| 5,342,346 | A | | 8/1994 | Honda et al. | |
| 5,348,548 | A | | 9/1994 | Meyer et al. | |
| 5,350,372 | A | | 9/1994 | Ikeda et al. | |
| 5,360,410 | A | | 11/1994 | Wacks | |
| 5,393,497 | A | | 2/1995 | Haber et al. | |
| 5,397,303 | A | | 3/1995 | Sancoff et al. | |
| 5,445,631 | A | | 8/1995 | Uchida | |
| 5,466,220 | A | | 11/1995 | Brenneman | |
| 5,478,337 | A | | 12/1995 | Okamoto et al. | |
| 5,526,853 | A | | 6/1996 | McPhee et al. | |
| 5,531,683 | A | | 7/1996 | Kriesel et al. | |
| 5,603,695 | A | | 2/1997 | Erickson | |
| 5,624,638 | A | | 4/1997 | Negrotti | |
| 5,636,660 | A | * | 6/1997 | Pfleiderer et al. | 137/550 |
| 5,855,575 | A | | 1/1999 | Solomon et al. | |
| 5,873,872 | A | | 2/1999 | Thibault et al. | |
| 5,876,372 | A | | 3/1999 | Grabenkort et al. | |
| 5,879,345 | A | | 3/1999 | Aneas | |
| 5,925,029 | A | | 7/1999 | Jansen et al. | |
| 5,928,213 | A | | 7/1999 | Barney et al. | |
| 5,944,709 | A | | 8/1999 | Barney et al. | |
| 5,954,696 | A | | 9/1999 | Ryan | |
| 6,003,566 | A | | 12/1999 | Thibault et al. | |
| 6,036,680 | A | | 3/2000 | Horne et al. | |
| 6,117,123 | A | | 9/2000 | Barney et al. | |
| 6,139,534 | A | | 10/2000 | Niedospial, Jr. et al. | |
| 6,224,346 | B1 | | 5/2001 | Denneburg | |
| 6,238,372 | B1 | | 5/2001 | Zinger et al. | |
| 6,355,023 | B1 | | 3/2002 | Roth et al. | |
| 6,364,865 | B1 | | 4/2002 | Lavi et al. | |
| 6,379,340 | B1 | | 4/2002 | Zinger et al. | |
| 6,409,708 | B1 | | 6/2002 | Wessman | |
| 6,474,375 | B2 | | 11/2002 | Spero et al. | |

FOREIGN PATENT DOCUMENTS

| | | | |
|---|---|---|---|
| EP | 0592 689 | | 11/1993 |
| FR | 3811 152 | | 10/1988 |
| WO | WO 89/00836 | A1 | 2/1989 |
| WO | WO 96/29113 | | 9/1996 |
| WO | WO 97/10156 | | 3/1997 |
| WO | WO09720536 | A1 | 6/1997 |
| WO | WO 97/20536 | | 6/1997 |
| WO | WO09802129 | A1 | 1/1998 |
| WO | WO 98/02129 | | 1/1998 |
| WO | WO 99/26581 | A1 | 6/1999 |

* cited by examiner

RECONSTITUTION DEVICE AND METHOD OF USE

BACKGROUND OF THE INVENTION

Many drugs administered to patients comprise a compound of medicament components mixed shortly before use. Oftentimes it is necessary to store these substances in separate containers until use. Reconstitution of the compound may require the mixing of a liquid-phase component and a solid-phase component, or the mixing of two liquid-phase components. Commonly, the solid-phase component is in powder form to permit stable storing of a component. The containers used to store these components may be constructed of glass, plastic, or other suitable material.

One way currently used to reconstitute materials requires a first component to be injected with a syringe into a container containing a second component. For example, a syringe having a needle attached thereto is inserted through the rubber membrane top of a container containing a first liquid-phase component. Thereafter, the first liquid-phase component is withdrawn into the syringe barrel. The needle is then removed from the liquid-phase component container. Subsequently, the needle of the syringe is inserted through the rubber membrane top of the second liquid-phase or solid-phase component container and the first liquid-phase component is injected from the syringe barrel into the second container. The second container is shaken to mix the components. Thereafter, a needle attached to a syringe is inserted through the rubber membrane top and the component mixture is drawn into the syringe barrel. The needle is removed from the container and the component mixture may then be administered.

An improvement to this process is the subject of U.S. Pat. No. 6,379,340, entitled "Fluid Control Device", which utilizes two opposing container receivers to grip and orient the containers. Spikes within the receivers penetrate the rubber membrane top of each container to establish communication with the interior of the containers when mounted on the receivers. Passageways within the spikes and a multi-position valve establish selective communication between the containers and to a syringe thereby allowing the user to reconstitute the drug according to a specific sequence of valve orientations. One shortcoming associated with this device requires the user must manipulate the valve in the correct sequence to reconstitute the drug. In addition, the liquid flowing from the spike and dropping into the solid phase container may cause turbulence and/or frothing on the surface of the fluid. Such frothing may generate a concern to the user that the reconstitution has not occurred correctly.

With respect to these devices, it is desirable to have a system capable of reconstituting a multiple component material using commercially available component storage containers. Additionally, it is desirable to have a reconstitution system wherein the operator may easily control the reconstitution. Furthermore it is desirable to reduce the frothing of the mixture of the solid and liquid phase components during the reconstitution process. It is, thus, also desirable to have a reconstitution device and method that reduces or eliminates the possibility of inadvertent needle sticks.

BRIEF SUMMARY OF THE INVENTION

The present application discloses a reconstitution device and method of reconstituting a multiple component material. The individual components of the multiple component material may include liquid-liquid phase mixtures and liquid-solid phase mixtures. Further, the containers housing the individual components may at, above, or below the pressure of the ambient atmosphere.

In one embodiment, a reconstitution device is disclosed and includes a first container receiver having a first component cannula disposed therein, the first component cannula having a withdrawal port and a first transfer port formed thereon, a second container receiver having a second component cannula disposed thereon, the second component cannula having a vent port and a second transfer port formed thereon, a device body coupling the first container receiver to the second container receiver and having a transfer lumen formed therein, the transfer lumen in fluid communication with the first and second transfer ports, a selectively sealing interface secured to the device body and in fluid communication with the withdrawal port, and a venting member in communication with the vent port through a vent lumen.

In an alternate embodiment, a reconstitution device is disclosed and includes a first container receiver having a first component cannula disposed therein, the first component cannula having a withdrawal port and a first transfer port formed thereon, a second container receiver having a second component cannula disposed thereon, the second component cannula having a vent port and a second transfer port formed thereon, a device body coupling the first container receiver to the second container receiver and having a transfer lumen formed therein, the transfer lumen in fluid communication with the first and second transfer ports, a telescoping extension positioned within the transfer lumen and configured to controllably extend into the first container receiver, a selectively sealing interface secured to the device body and in fluid communication with the withdrawal port, and a venting port in communication with the vent port through a vent lumen.

In another embodiment, a reconstitution device is disclosed and includes a first container receiver having a first component cannula configured to be positioned proximate to a base of a container attached thereto disposed therein, the first component cannula having a withdrawal port and a first transfer port formed thereon, a second container receiver having a second component cannula disposed thereon, the second component cannula having a vent port and a second transfer port formed thereon, a device body coupling the first container receiver to the second container receiver and having a transfer lumen formed therein, the transfer lumen in fluid communication with the first and second transfer ports, a selectively sealing interface secured to the device body and in fluid communication with the withdrawal port, and a venting port in communication with the vent port through a vent lumen.

The present application also discloses a method of reconstituting a multiple component material and includes coupling a second container having a second material therein to a reconstitution device, inverting the reconstitution device such that the second container is inverted, coupling a first container having a first material therein to the reconstitution device, creating a pressure differential between the second container and the first container, transferring the second material from the second container to the first container, mixing the first and second material within the first container to form a mixed material, inverting the reconstitution device such that the first container inverted, and withdrawing the mixed material from the reconstitution device.

BRIEF DESCRIPTION OF THE DRAWINGS

The apparatus of the present invention will be explained in more detail by way of the accompanying drawings, wherein.

DETAILED DESCRIPTION OF THE INVENTION

Disclosed herein is a detailed description of various embodiments of the invention. This description is not to be taken in a limiting sense, but is made merely for the purpose of illustrating the general principles of the invention. The overall organization of the present detailed description is for the purpose of convenience only and is not intended to limit the invention.

The reconstitution device disclosed herein is used to facilitate the transfer of components between separate component containers. More particularly, the reconstitution device permits the user to create a pressure differential between a first component container and a second component container thereby permitting the efficient transfer of materials between the component containers. In one embodiment, the reconstitution device enables the operator to transfer materials from commercially available component containers with reduced turbulence and increased user safety while greatly reducing the likelihood of material contamination and errors in the attachment of the containers to the reconstitution device. As those skilled in the art will appreciate, the reconstitution device is simple and inexpensive to manufacture and may be capable of transferring material between and extracting material from a variety of existing component containers. It is anticipated as being within the scope of the present invention to produce a reconstitution device capable of functionally coupling with a plurality of component containers in a plurality of sizes.

Figure 1:
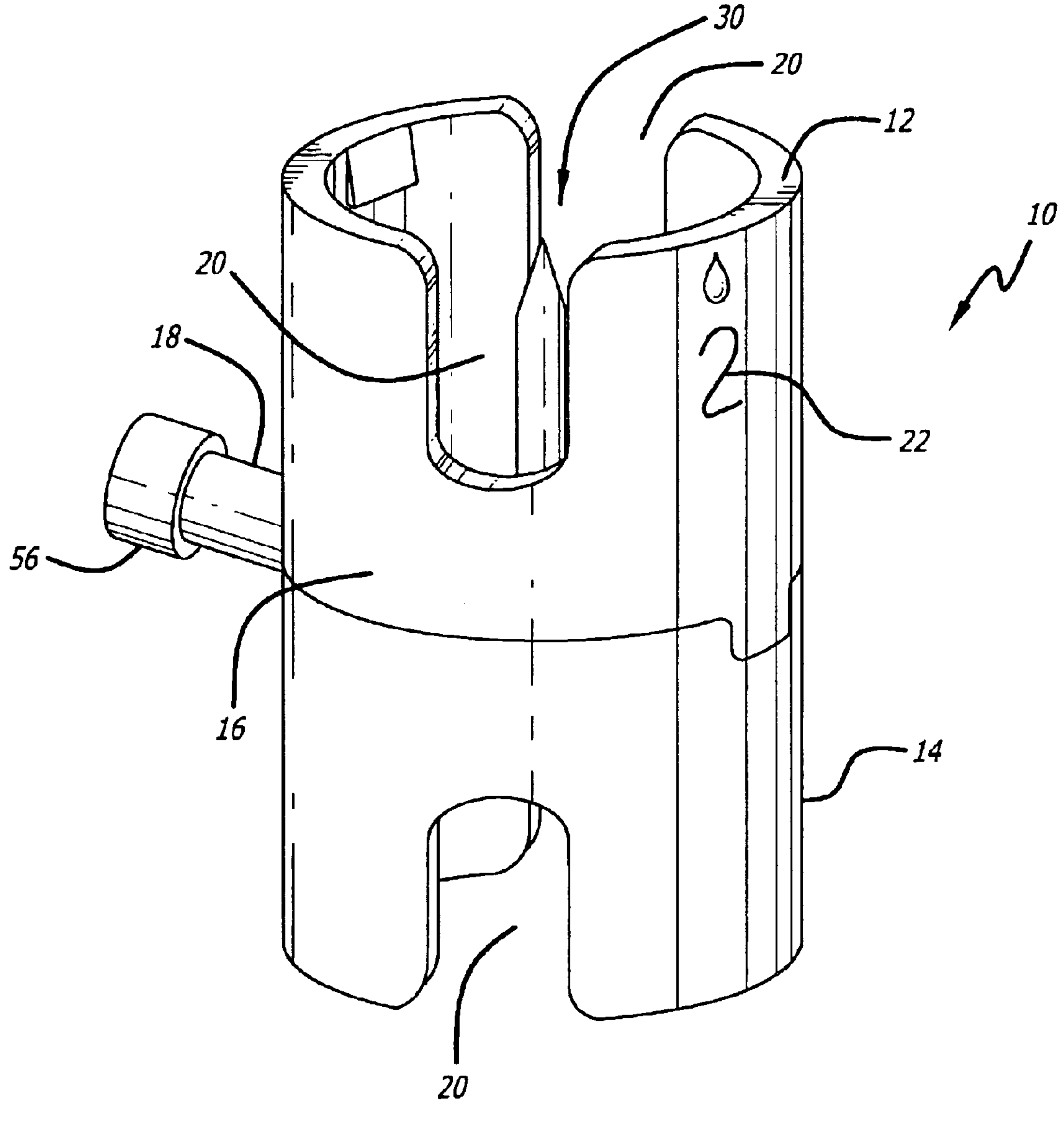
FIG. 1 is a perspective view of an embodiment of a reconstitution device.

FIG. 1 shows an embodiment of a reconstitution device 10 for reconstituting a multiple component material. In the illustrated embodiment, the reconstitution device 10 includes a first container receiver 12, a second container receiver 14, and device body 16 positioned therebetween. A selectively sealed withdrawal interface 18 extends from the device body 16. As shown, the reconstitution device 10 includes indentations 20 formed on the first and second container receivers 12, 14, respectively. In an alternate embodiment, the reconstitution device 10 may include at least one indentation 20 formed on the first container receiver 12, the second container receiver 14, or both. Optionally, the reconstitution device 10 may be manufactured without indentations 20.

In the illustrated embodiment, at least one assembly aid 22 is imprinted or otherwise disposed on at least one of the component receivers 12, 14, respectively, and/or the device body 16, thereby instructing the user on the proper sequence of container attachment. Exemplary assembly aids 22 include, without limitation, numbers, letters, words, and symbols including droplets. In another embodiment, the reconstitution device 10 may be manufactured without an assembly aid 22. The first receiver 12 and second receiver 14 may be color coded or manufactured of materials of different colors corresponding to or assisting the user in connecting the proper container to the to the proper container receiver. The reconstitution device 10 may be manufactured from polycarbonate. Optionally, the reconstitution device 10 may also be constructed of a plurality of materials, including, without limitation, polyethylene, polypropylene, polystyrene, or a like material.

Figure 2:
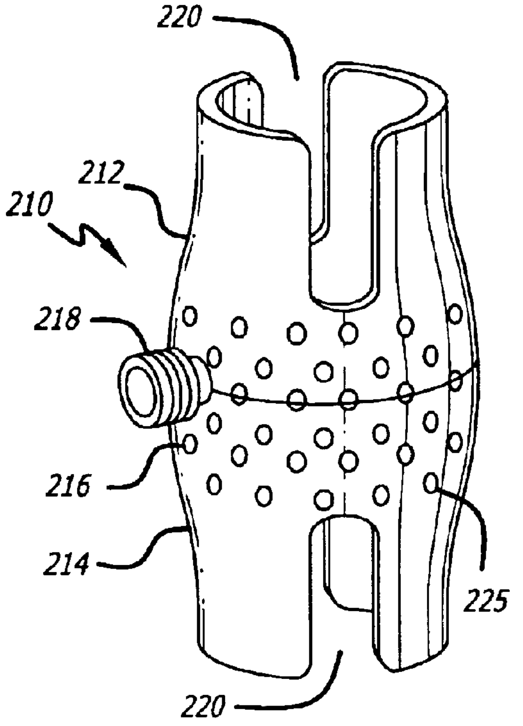
FIG. 2 is a perspective view of another embodiment of a device body of a reconstitution device having a gripping member disposed thereon.

FIGS. 2–5 show various alternate embodiments of a device body 16 of a reconstitution device 10 having an ergonomic or gripping surface positioned thereon. As shown in FIG. 2, the reconstitution device 210 includes a first container receiver 212, a second container receiver 214, and device body 216 positioned therebetween. In the illustrated embodiment, the device body 216 is ergonomically formed to fit comfortably within the hand of an operator. For example, in one embodiment, the device body 216 may be circular. In an alternate embodiment, the device body 216 may be oval or non-circular. A selectively sealed withdrawal interface 218 extends from the device body 216. The device body 216 includes at least one gripping member 225 thereon. Exemplary gripping members 225 include, without limitation, bumps, indentations, lines, tabs, or other devices configured to provide secure handling of the device body 210. In one embodiment, the gripping members 225 are formed on the device body 216. In an alternate embodiment, the gripping members 225 are coupled to or attached to the device body 216. The reconstitution device 210 includes indentations 220 formed on the first and second container receivers 212, 214, respectively. In an alternate embodiment, the reconstitution device 210 may include at least one indentation 220 formed on the first container receiver 212, the second container receiver 214, or both. Optionally, the reconstitution device 210 may be manufactured without indentations 220.

Figure 3:
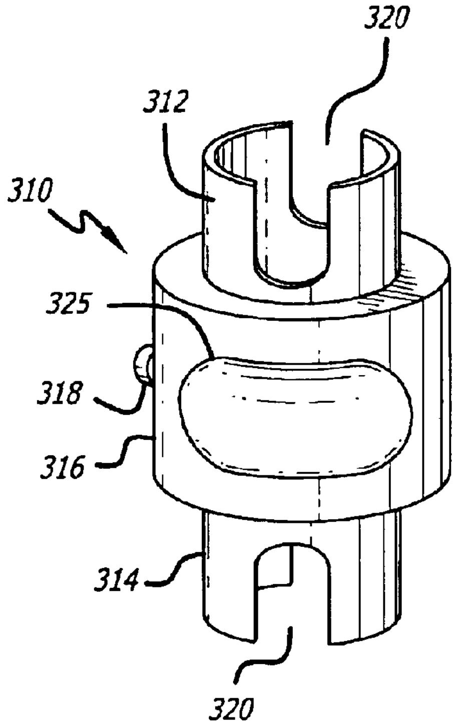
FIG. 3 is a perspective view of another embodiment of a device body of a reconstitution device having a gripping channel partially traversing the device body.

FIG. 3 shows an alternate embodiment of a reconstitution device 310 having a first container receiver 312, a second container receiver 314, and device body 316 positioned therebetween. A selectively sealed withdrawal interface 318 extends from the device body 316. The device body 316 includes at least one gripping channel 325 partially traversing the device body 316. The reconstitution device 310 includes indentations 320 formed on the first and second container receivers 312, 314, respectively. In an alternate embodiment, the reconstitution device 310 may include at least one indentation 320 formed on the first container receiver 312, the second container receiver 314, or both. Optionally, the reconstitution device 310 may be manufactured without indentations 320.

Figure 4:
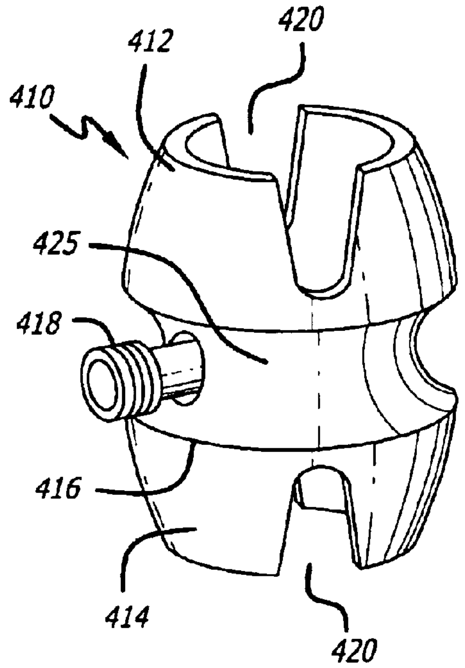
FIG. 4 is a perspective view of another embodiment of a device body of a reconstitution device having a gripping channel traversing the device body.

FIG. 4 shows another embodiment of a reconstitution device 410 having a first container receiver 412, a second container receiver 414, and device body 416 positioned therebetween. A selectively sealed withdrawal interface 418 extends from the device body 416. The device body 416 includes at least one gripping channel 425 laterally traversing the device body 416. The reconstitution device 410 includes indentations 420 formed on the first and second container receivers 412, 414, respectively. In an alternate embodiment, the reconstitution device 410 may include at least one indentation 420 formed on the first container receiver 412, the second container receiver 414, or both. Similar to the embodiments illustrated above, the reconstitution device 410 may be manufactured without indentations 420.

Figure 5:
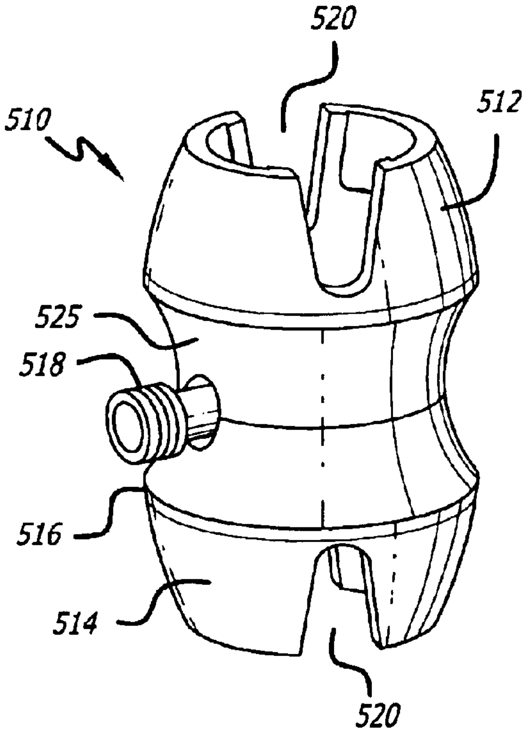
FIG. 5 is a perspective view of another embodiment of a device body of a reconstitution device having a gripping channel traversing the device body.

FIG. 5 shows another embodiment of a reconstitution device 510 having a first container receiver 512, a second container receiver 514, and device body 516 positioned therebetween. A selectively sealed withdrawal interface 518 extends from the device body 516. The device body 516 includes at least one gripping channel 525 longitundinally and laterally traversing the device body 516. The reconstitution device 510 includes indentations 520 formed on the first and second container receivers 512, 514, respectively. In an alternate embodiment, the reconstitution device 510 may include at least one indentation 520 formed on the first container receiver 512, the second container receiver 514, or both. Similar to the embodiments illustrated above, the reconstitution device 510 may be manufactured without indentations 520.

Figure 6:
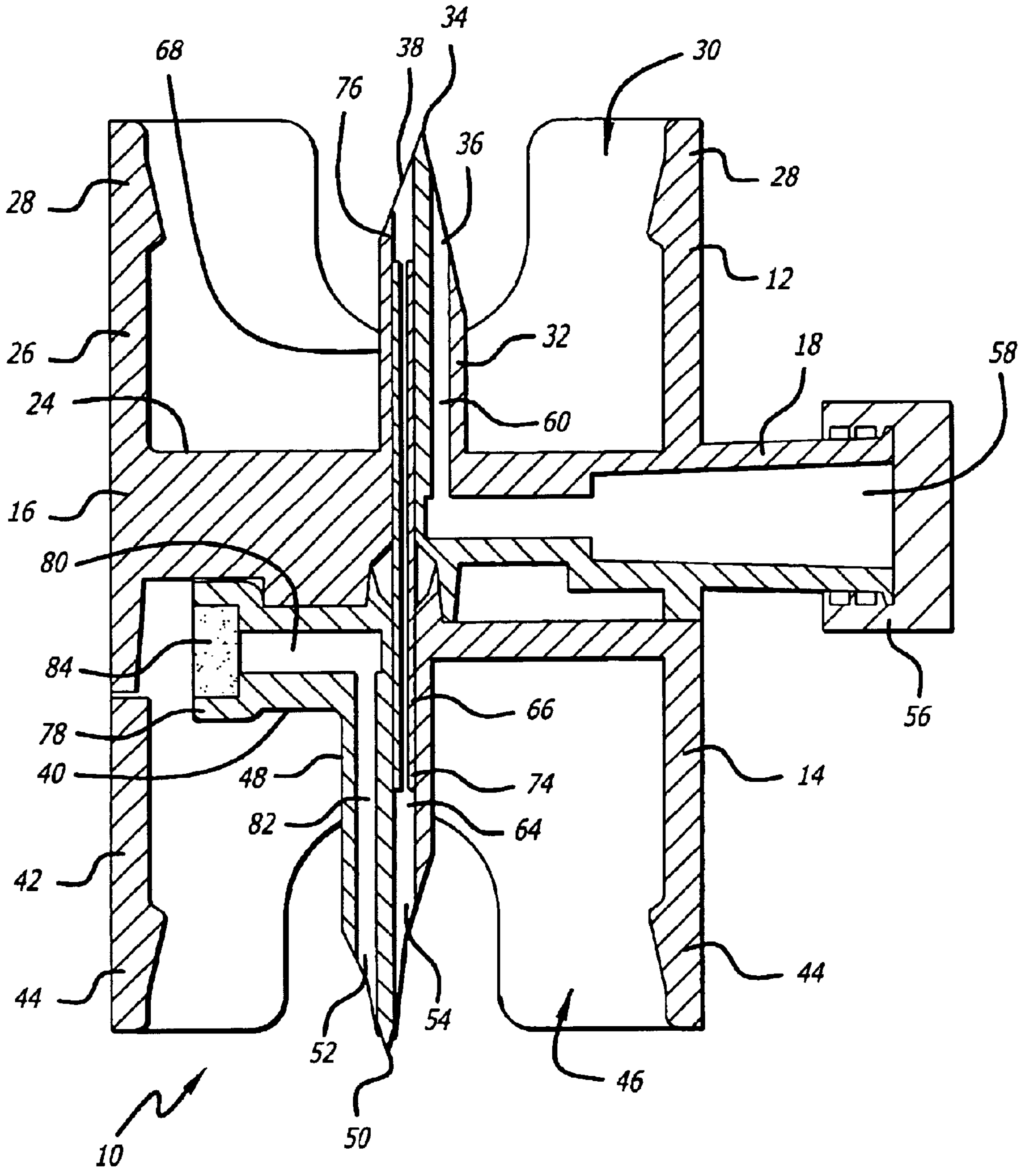
FIG. 6 is a side cross-sectional view of the reconstitution device illustrated in FIG. 1.

As shown in FIGS. 1 and 6, the reconstitution device 10 further includes a first container stop 24 and first container collar 26 having a first container locking member 28 positioned thereon. A first container orifice 30 is formed within the first container collar 26 of the first container receiver 12. A first component cannula 32 is positioned within the first container orifice 30. The first component cannula 32 includes a first pointed tip 34 and includes a first component withdrawal port 36 and a first transfer port 38 formed thereon.

The second container receiver 14 comprises a second container stop 40 and a second container collar 42 having a second container locking member 44 positioned thereon. A second container orifice 46 is formed within the second container receiver 14. A second component cannula 48 is positioned within the second container orifice 46. The second component cannula 48 includes a second pointed tip 50 includes a vent port 52 and a transfer port 54 formed thereon.

Interposed between the first container receiver 12 and the second container receiver 14 is the device body 16 having with interface 18 positioned thereon. Selectively sealing the interface 18 is a removable cap 56. The removable cap 56 may be constructed of several materials such as a polymeric material or a membrane type material.

As shown in FIG. 6, the withdrawal interface 18 forms a withdrawal orifice 58, which is in communication with the withdrawal port 36 through withdrawal lumen 60 located within the first cannula 32. In an embodiment, a filter 59 is disposed within the withdrawal interface 18 to filter solution flowing out through the orifice 58. A transfer lumen 64 extends within the device body 16 and couples the first cannula 32 and second cannula 48. As a result, the transfer port 38 located of the first container receiver 12 is in fluid communication with the transfer port 54 of the second container receiver 14 through the transfer lumen 64.

Figure 7:
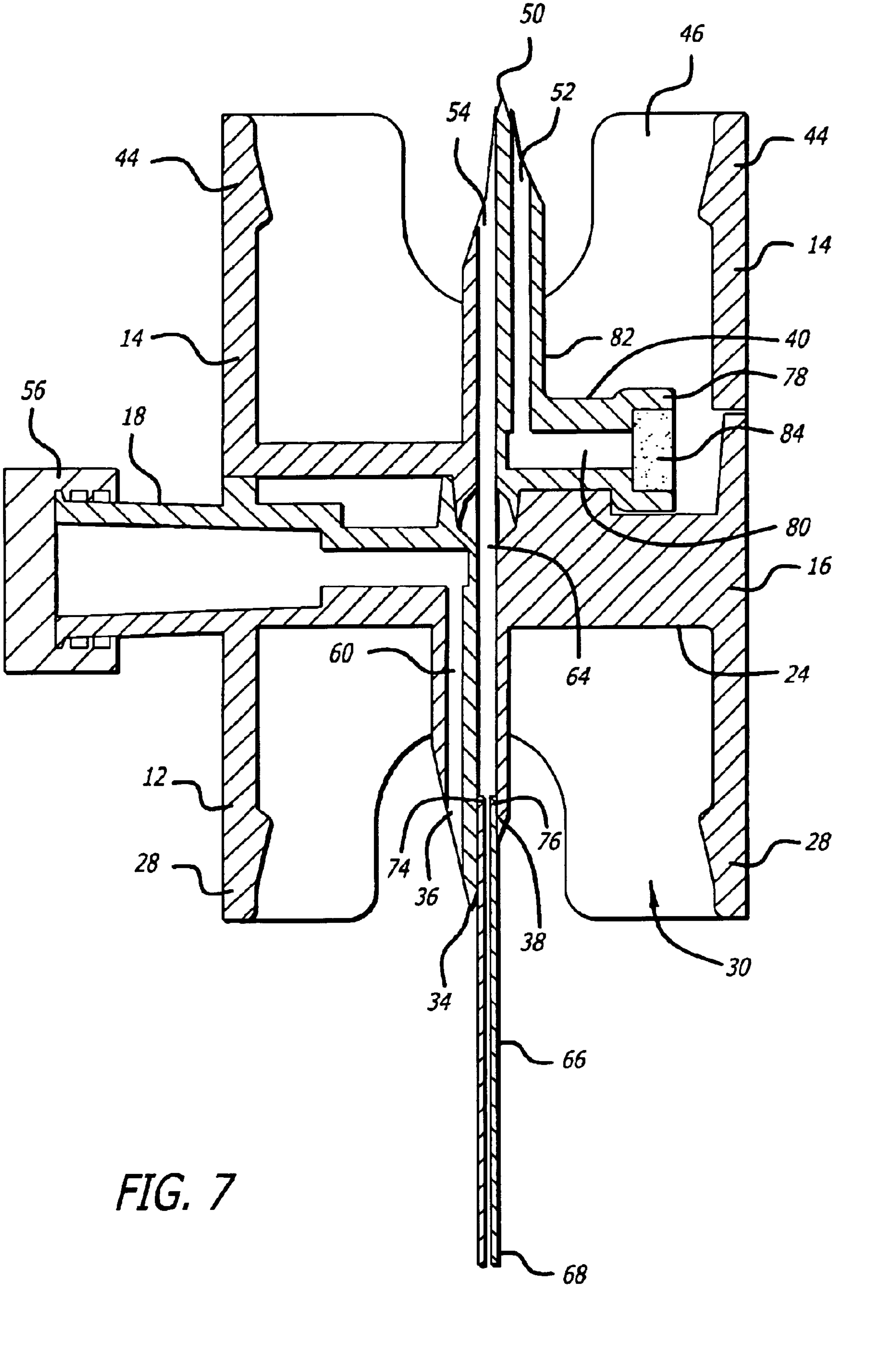
FIG. 7 is a side cross-sectional view of the reconstitution device illustrated in FIG. 1 with an extension tube in an extended position.

Also shown in FIGS. 6 and 7, a telescoping extension 66 is slidably disposed within the transfer lumen 64. FIG. 6 shows the telescoping extension 66 positioned within the transfer lumen 64. FIG. 7 shows the telescoping extension 66 extending from the transfer lumen 64 wherein an extension tip 68 is capable of being positioned proximate a base of a container (not shown) coupled to the first container receiver 12. In one embodiment, a base 74 of the extension 66 positioned within the transfer lumen 64 is flared outwardly and configured to engage a stop 76 formed within the first cannula 32 along the transfer lumen 64.

Referring back to FIG. 6, the venting port 78 forms a vent orifice 80 which is in communication with the vent port 52 through vent lumen 82 located within the second component cannula 48. In a preferred embodiment, a filter 84 is disposed within the venting port 78. In a further embodiment, the filter 84 is sterile and configured to filter air that enters the vent orifice 80 and lumen 82.

Figure 8:
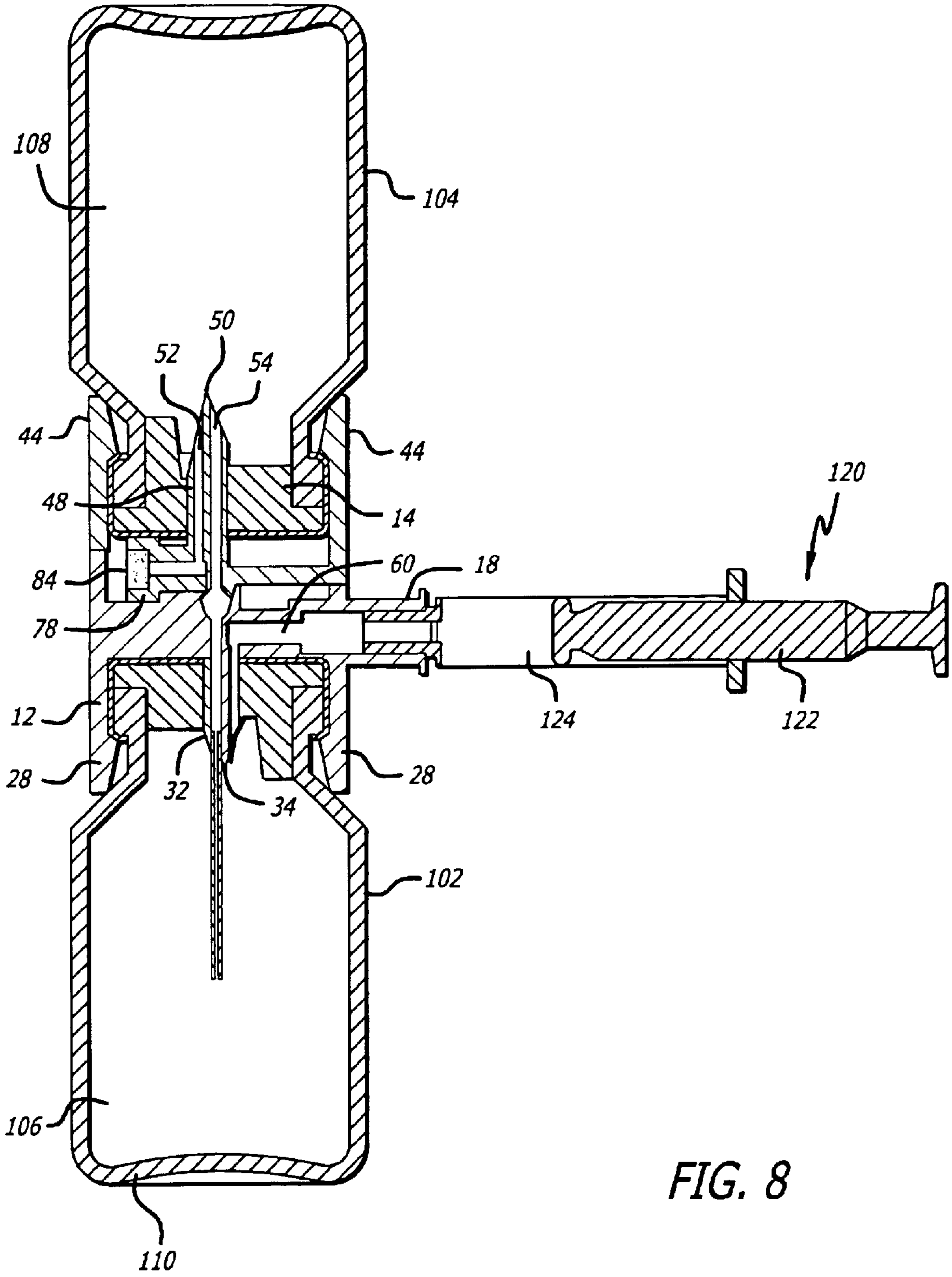
FIG. 8 is a side cross sectional view of the reconstitution device of FIG. 7 attached to a first container, a second container, and a withdrawal syringe coupled thereto.

Referring to FIGS. 7 and 8, a first container 102 is positioned within the first container receiver 12 such that container locking members 28 secure the first container 102 within the container orifice 30. Similarly, a second container 104 is positioned within the second container receiver 14 such that container locking members 44 secure the second container 104 within the second container orifice 46. As shown, locating the first container 102 within the first container receiver 12 results in the first pointed tip 34 of the first cannula 32 piercing the sealing material (not shown) of the first container 102, thereby positioning the first cannula 32 within the interior 106 of the first container 102. Likewise, locating the second container 104 within the second container receiver 14 results in the second pointed tip 50 of the second cannula 48 piercing the sealing material (not shown) of the second container 104, thereby positioning the second cannula 48 within the interior 108 of the second container 104. The first cannula 32 and the second cannula 48 may be manufactured from a plurality of materials, including, without limitation, polyethylene, polypropylene, polystyrene, stainless steel, or a like material.

Various methods for reconstituting multiple component materials are also disclosed herein. More specifically, the methods disclosed herein permit the transfer of materials from multiple component containers and the reconstitution of a multiple component material. In one embodiment, an operator-controlled sequence of coupling the individual component containers to the reconstitution device utilizes an existing pressure differential to effect the transfer of material between the containers and the withdrawal of the reconstituted formulation from the containers.

One method of using the reconstitution device is illustrated in FIGS. 1 and 6–8 and utilizes a negative pressure differential between the first and second component containers 102, 104, formed during the manufacture of the first container 102 to effect a material transfer. As shown, the reconstitution device 10 is oriented such that the second cannula 48 is extending downwardly (see FIG. 6). The reconstitution device 10 is lowered onto a second container 104 such that the second container 104 is positioned within the second container receiver 14. The second cannula 48 is made to penetrate the top of the second container 104 and is in fluid communication with the material stored therein. The locking members 44 snap about the top of the second container 104 to detachably couple the second container 104 to the reconstitution device 10. In one embodiment, the second container 104 is filled with a liquid component.

The tip 50 of the second cannula 48 is positioned within the interior area 108 of the second container 104 such that the transfer port 54 is positioned closely adjacent the container seal (not shown) to facilitate the transfer of material from the second container 104 when the locking members 44 secure the second container 104. The extension 66 remains positioned within the transfer lumen 64.

Figure 9:
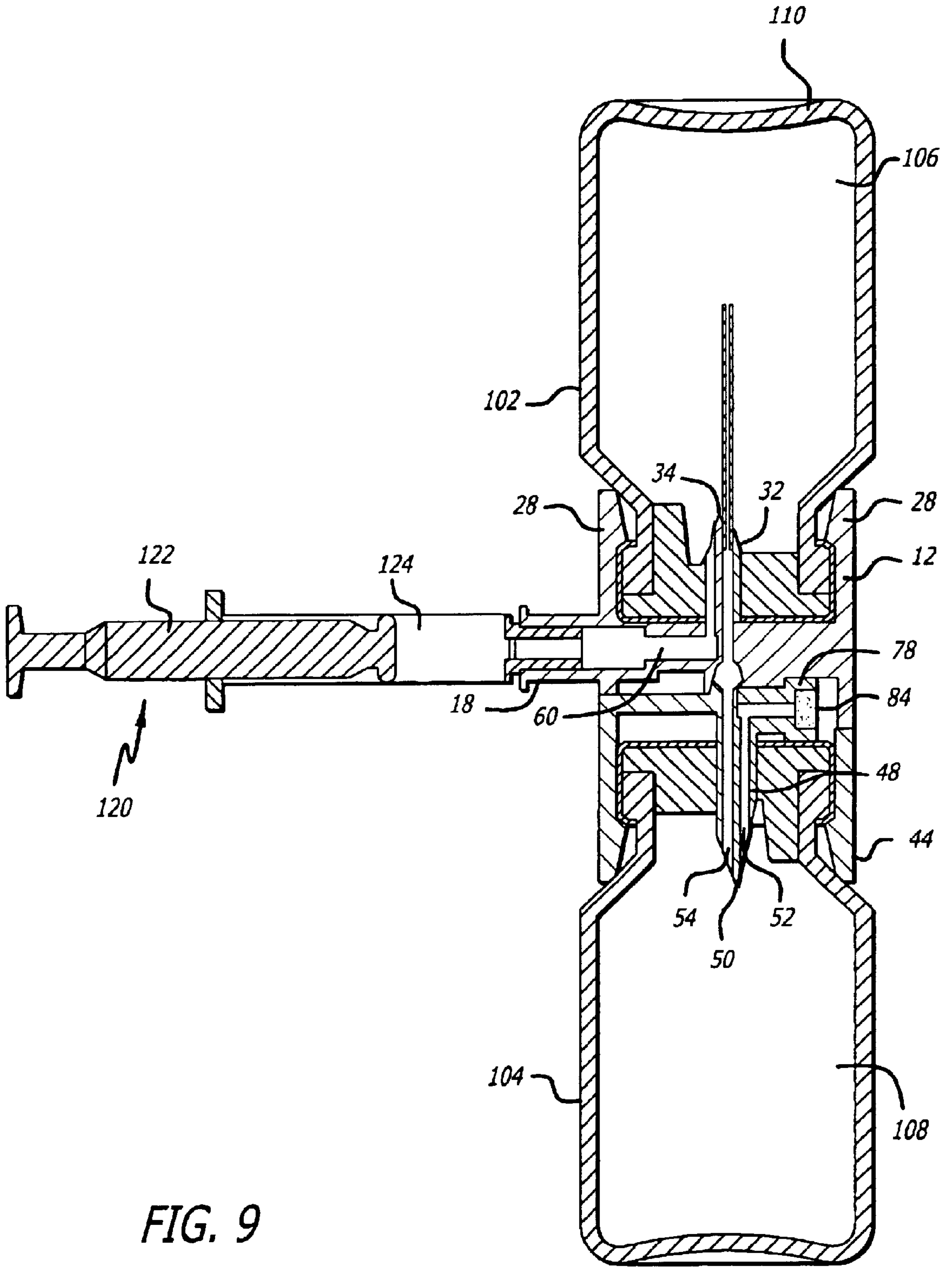
FIG. 9 is a side cross sectional view of the reconstitution device of FIG. 8 inverted and having attached to a first container, a second container, and a withdrawal syringe coupled thereto.
Figure 10:
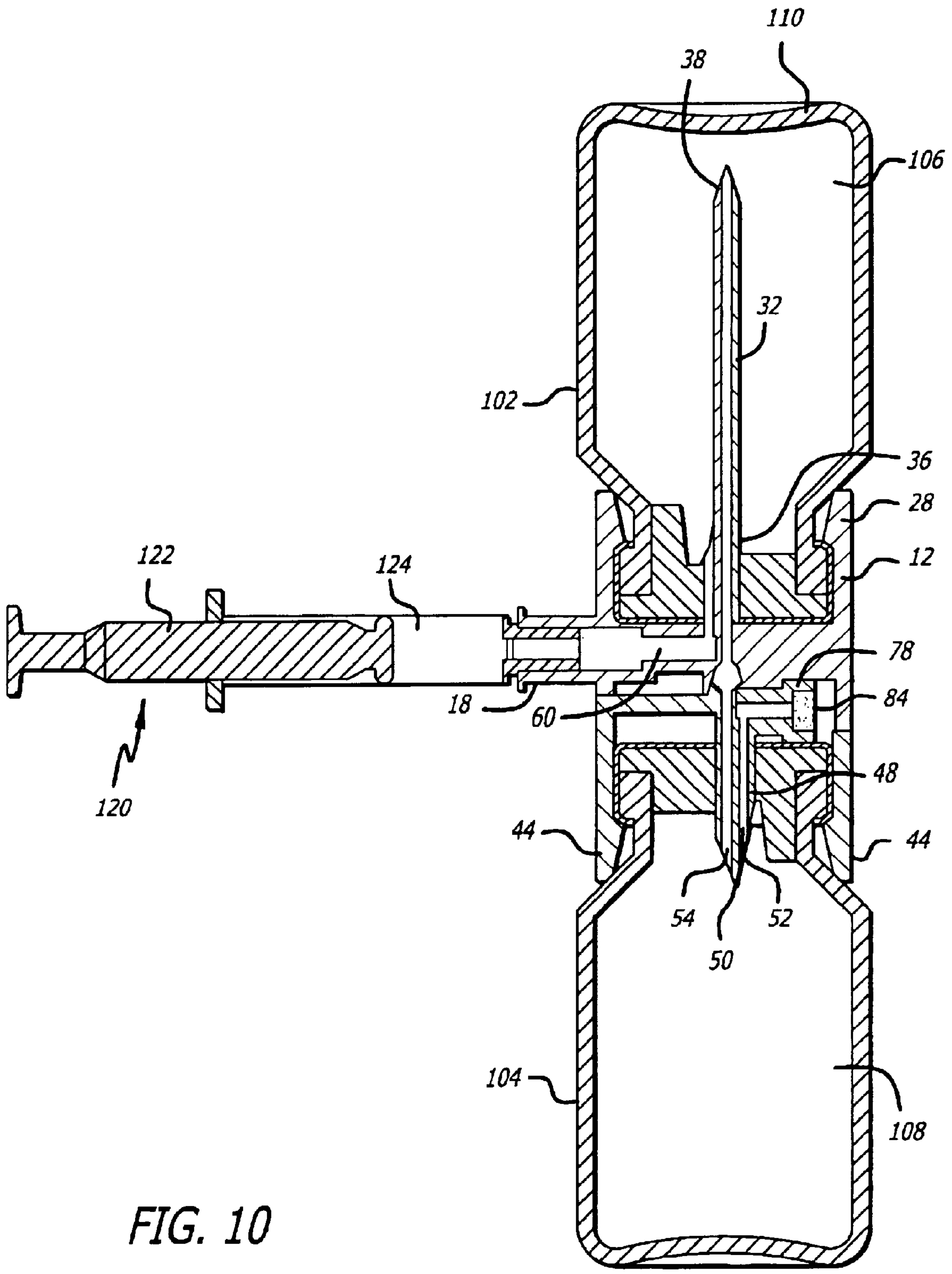
FIG. 10 is a side cross sectional view of another embodiment of a reconstitution device having an extended first cannula positioned within a first container, and a second container and withdrawal syringe coupled thereto.

Referring to FIGS. 7–9, the reconstitution device 10 is then reoriented such that the second cannula 48 extends in an upward direction and the first cannula 32 extends in a downward direction (see FIG. 7). The reconstitution device 10 is lowered onto the first container 102 such that the first container 102 is positioned within the first container receiver 12. The first cannula 32 is made to penetrate the top of the first container 102 and is in fluid communication with the material stored therein. The locking members 28 engage the top of the first container 102 to detachably couple the first container 102 to the reconstitution device 10. In one embodiment, the first container 102 is filled with a solid component. The tip 34 of the first cannula 32 is positioned within the interior 106 the first container 102 such that the withdrawal port 36 is positioned closely adjacent to the seal of the first container 102 to facilitate transfer of the contents of the first container 102 as the locking members 28 secure the first container 102.

The penetration of the first cannula 32 into the first container 102 results in the creation of a negative pressure differential between the first and second containers 102, 104, respectively, and effectuates the transfer of material from the second container 104 through the transfer lumen 64 to the first container 102. During the insertion of the first cannula 32 into the first container 102 air flows into the venting port 78 and through the lumen 82, replacing the volume of fluid flowing between the first and second containers 102, 104 through the transfer lumen 64. As the air flows through the filter 84, the air is filtered to remove any contaminating particles. The second cannula 48 is configured such that the vent port 52 on the second cannula 48 is located farther into the interior 108 of the container 104 than the transfer port 54, thereby permitting for all or substantially all the material within the second container 104.

As the material flows from the second container 104 to the first container 102 through the transfer lumen 64, the material flow engages the extension 66 positioned within the transfer lumen 64. The resultant drag of the material flow pushes the extension 66 thereby deploying the extension 66 from the transfer lumen 64. The extension 66 extends into the interior 106 of the first container 102 toward the base 110 of the container (see FIG. 8). If the height of the interior 106 of the container 102 is less than the extension 66 the extension 66 will not fully extend. If the height of the interior of the container 102 is greater than the extension 66 the extension 66 fully extends until the contact the flared end 74 of the extension 66 engages the stop 76 thereby maintaining the flared end 74 of the extension 66 within the first cannula 32. The material flow exiting from the tip 68 of the extension 66 when positioned closely adjacent to or contacting the base 110 of the first container 102 producing less turbulence and frothing of the resulting mixture.

Once the material has been transferred from the second container 104 to the first container 102 and mixing and/or dissolution has occurred, the reconstitution device 10 may be oriented such that the first cannula 32 extends upwardly (see FIG. 9). The cap 56 (see FIG. 7) may be removed from the withdrawal interface 18 and a withdrawal syringe 120 connected to the withdrawal interface 18. Pulling back on the plunger 122 creates a negative pressure within the syringe body 124 and effectuates the transfer of material from the first container 102 through the withdrawal port 36 and withdrawal lumen 60 and into the syringe 120. Because the tip 68 extends farther into the interior 106 of the first container 102 than the withdrawal port 36 the contents of the first container 102 will be completely withdrawn. Air flows into the venting port 78, through the second container 104, into transfer lumen 64 and enters the first container 102 through extension 66, thereby replacing the volume of material being withdrawn. The tip 68 of the extension 66 is disposed higher within the first container 102 than the upper surface of the mixture, reducing the amount of bubbles or froth produced therein. In one embodiment, the air flowing through the venting port 78 is filtered by filter 84, thereby removing contaminants within the air and reducing the likelihood of contamination of the material.

In an alternate embodiment, the first container 102 and second container 104 may be packaged with the reconstitution device 10. As the size and volume of the first and second containers 102, 104 are known, the first cannula 32 may be configured to extended into the interior 106 of the first container 102 such that the tip 34 of the first cannula 32 is positioned adjacent to the base 110 of the first container 102. As a result, the extension 66 may be eliminated. The cannula 32 is also configured such that the withdrawal port 36 is adjacent the base of the interior 106 of the first container 102 to facilitate the complete withdrawal of material therefrom.

In closing, it is noted that specific illustrative embodiments of the reconstitution device have been disclosed hereinabove. However, it is to be understood that the reconstitution device is not limited to these specific embodiments. Accordingly, the invention or methods of practicing the invention are not limited to the precise embodiments described in detail hereinabove. Those skilled in the art will appreciate the benefits advanced by the present invention. For example, no material transfer between the containers will occur until a pressure differential has been created between the containers. Also, the transfer of material between the containers and withdrawal of material into an applicator occurs within a sealed environment. As a result, the likelihood of contamination is greatly reduced. Further, with respect to the claims, it should be understood that any of the claims described below can be combined for the purposes of the invention.

What is claimed is:

1. A reconstitution device, comprising:

a first container receiver having a first component cannula disposed therein, the first component cannula having a withdrawal port and a first transfer port formed thereon;

a second container receiver having a second component cannula disposed thereon, the second component cannula having a vent port and a second transfer port formed thereon;

a device body coupling the first container receiver to the second container receiver and having a transfer lumen formed therein, the transfer lumen in fluid communication with the first and second transfer ports;

a telescoping extension positioned within the transfer lumen and configured to controllably extend into the first container receiver;

a selectively sealing interface secured to the device body and in fluid communication with the withdrawal port; and a venting member in communication with the vent port through a vent lumen.

2. The device of claim 1 wherein the first cannula is configured to be positioned proximate to a base of a container attached thereto.

3. The device of claim 2 wherein the withdrawal port is positioned proximate to the device body.

4. The device of claim 1 further comprising a first container stop and a first container collar both defining a first container orifice.

5. The device of claim 1 further comprising at least one first container locking member positioned on the first container collar and configured to detachably couple a first container to the reconstitution device.

6. The device of claim 1 further comprising a second container stop and a second container collar both defining a second container orifice.

7. The device of claim 1 further comprising at least one second container locking member positioned on the second container collar and configured to detachably couple a second container to the reconstitution device.

8. The device of claim 1 further comprising a removable cap configured detachably couple to the selectively sealing interface.

9. The device of claim 1 further comprising a filter secured to the venting port and configured to filter air traversing therethrough.

10. The device of claim 1 further comprising a extension stop positioned within the transfer lumen and configured to retain at least a portion of the telescoping extension within the transfer lumen.

11. A reconstitution device, comprising:

a first container receiver having a first component cannula configured to be positioned proximate to a base of a container attached thereto disposed therein, the first component cannula having a withdrawal port and a first transfer port formed thereon;

a second container receiver having a second component cannula disposed thereon, the second component cannula having a vent port and a second transfer port formed thereon;

a device body coupling the first container receiver to the second container receiver and having a transfer lumen formed therein, the transfer lumen in fluid communication with the first and second transfer ports;

a telescoping extension positioned within the transfer lumen and configured to controllably extend into the first container receiver;

a selectively sealing interface secured to the device body and in fluid communication with the withdrawal port; and a venting member in communication with the vent port through a vent lumen.

12. The device of claim 1 further comprising at least one gripping member positioned on the device body.

13. The device of claim 1 further comprising at least one gripping channel formed on the device body.

14. The device of claim 1 wherein the device body is oval.

15. The device of claim 14 further comprising at least one gripping member positioned on the device body.

16. The device of claim 1 wherein the device body is non-circular.

17. The device of claim 16 further comprising at least one gripping member positioned on the device body.

* * * * *